US00PP17297P2

(12) United States Plant Patent
Danziger

(10) Patent No.: US PP17,297 P2
(45) Date of Patent: Dec. 19, 2006

(54) ***SOLIDAGO* PLANT NAMED 'DANSOLITLEM'**

(50) Latin Name: *Solidago hybrida*
Varietal Denomination: Dansolitlem

(76) Inventor: Gabriel Danziger, P.O. Box 24, Beit Dagan (IL)

( * ) Notice: Subject to any disclaimer, the term of this patent is extended or adjusted under 35 U.S.C. 154(b) by 0 days.

(21) Appl. No.: 11/206,335

(22) Filed: Aug. 17, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—Annette H Para

(57) ABSTRACT

A new and distinct *Solidago* plant named 'Dansolitlem' particularly characterized by having compact basal branching habit and an inflorescence comprised of closely packed light yellow colored flowers.

2 Drawing Sheets

Genus: *Solidago*. Species: *hybrida*.
Denomination: Dansolitlem.

BACKGROUND OF THE INVENTION

The present invention relates to a new and distinct cultivar of goldenrod plant, botanically known as *Solidago hybrida* and hereinafter referred to by the cultivar name 'Dansolitlem'.

Goldenrods are members of the sunflower family (Asteraceae). There are approximately 100 species of *Solidago* plants found in North America, most of which are geographically located in the East. Goldenrods are perennial plants that commonly grow along stream banks, ditches, roadsides and other areas where the soil is moist and rich.

The new cultivar originated from a cross made in an open pollinated program in Moshav Mishmar Hashiva, Israel. The female parent is an unreleased and unpatented seedling selection named 3-py-35 which arose and was retained from the breeding program. The male is unknown. 'Dansolitlem' was discovered and selected by the inventor, Gabriel Danziger, as a flowering plant within the progeny of the stated cross in a controlled environment in Moshav Mishmar Hashiva, Israel.

Asexual reproduction of the new cultivar was first performed by the inventor in Moshav Mishmar Hashiva, Israel, using stem cuttings. The inventor has determined that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Dansolitlem' which in combination distinguish this *Solidago* as a new and distinct cultivar:

1. Inflorescence comprised of closely packed light yellow colored flowers
2. Overall height including flowers of 30 cm–35 cm
3. Compact basal branching habit Of the many commercial cultivars known to the inventor, the most similar in comparison to Dansolitlem is the cultivar

*Solidago* 'Solid Gold' (unpatented). Both 'Solid Gold' and 'Dansolitlem' exhibit small yellow flowers. However, 'Solid Gold' achieves a height including the flowers of 20 cm to 25 cm and is therefore shorter than 'Dansolitlem'.

Dansolitlem has not been observed under all possible environmental conditions. The phenotype of the new cultivar may vary significantly with variations in environment such as temperature, light intensity, and day length without any change in the genotype of the plant.

The following observations, measurements and values describe the new cultivars grown in Moshav Mishmar Hashiva, Israel under conditions which closely approximate to those generally used in commercial practice.

BRIEF DESCRIPTION OF THE DRAWINGS

The accompanying photographic drawings illustrate the overall appearance of the new *Solidago*, 'Dansolitlem' showing the colors as true as is reasonably possible with colored reproductions of this type.

The drawing labeled as FIG. 1 illustrates a whole plant of 'Dansolitlem'. The plant in the drawing is growing in a 1 gallon container and is approximately 10 months old from a rooted cutting.

Figure 1:
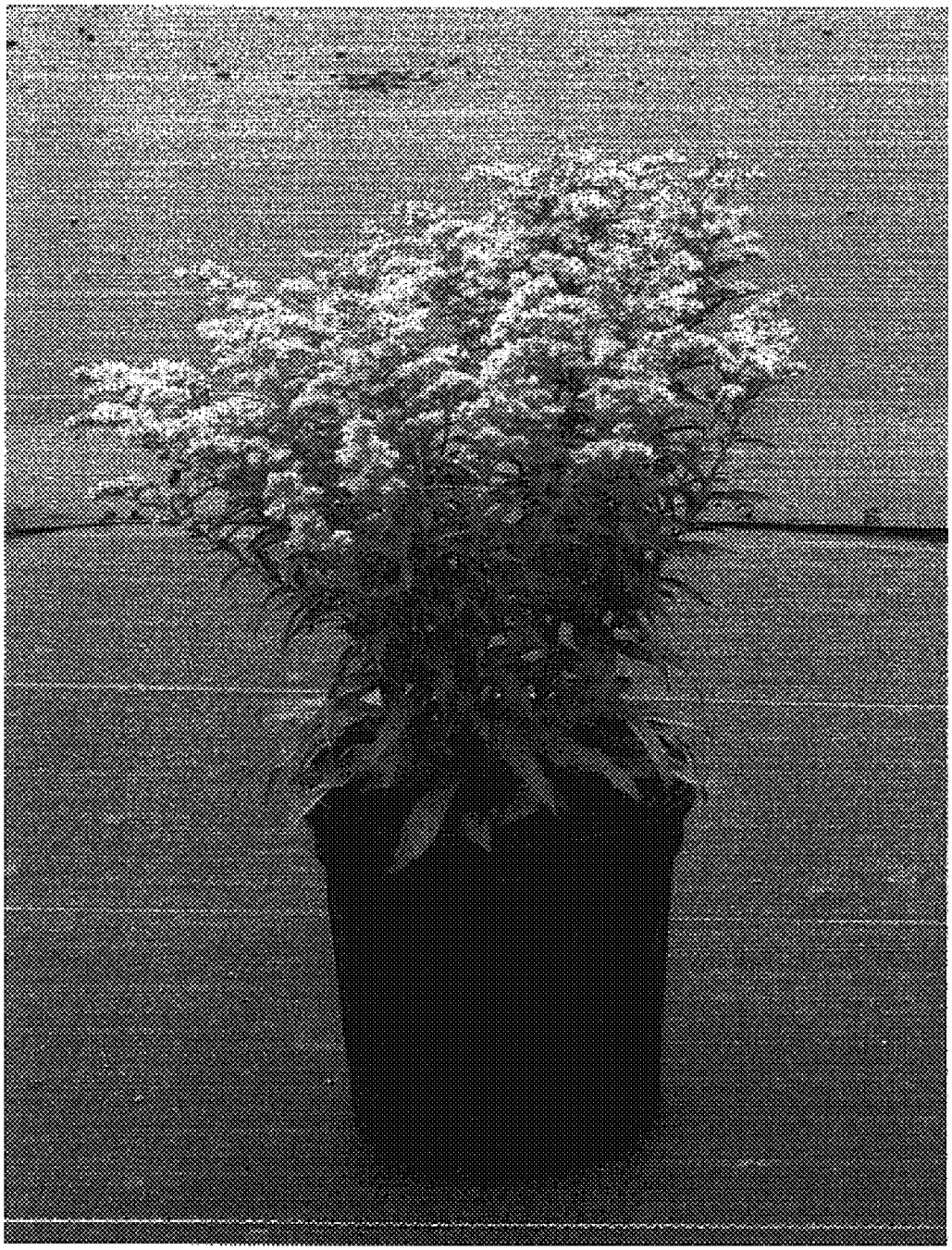
Figure 2:
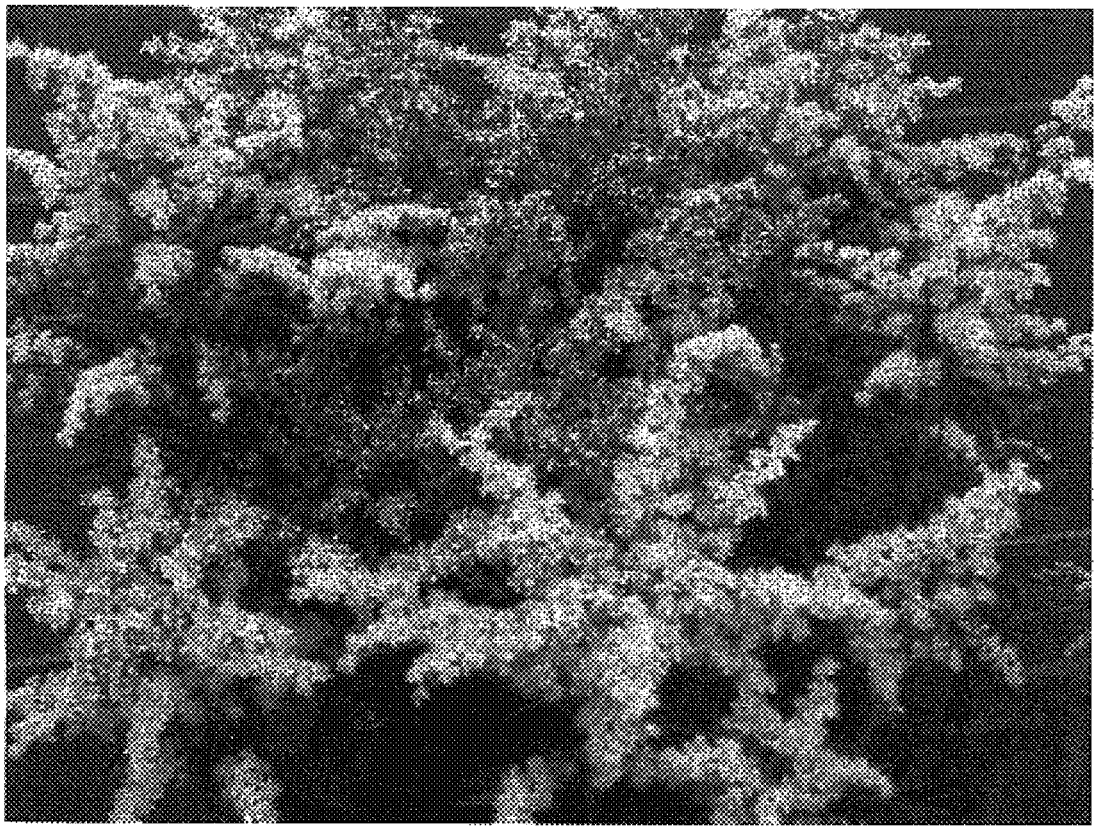

The drawing labeled as FIG. 2 illustrates a close up view of the inflorescence of 'Dansolitlem'.

DETAILED BOTANICAL DESCRIPTION

The following observations, measurements and values describe the new cultivar as grown in Moshav Mishmar Hashiva, Israel under conditions which closely approximate those generally used in commercial practice. Color references are made to The Royal Horticultural Society Colour Chart (R.H.S.) 2001, except where general colors of ordinary significance are used. Color values were taken under daylight conditions at approximately noon in Moshav Mishmar Hashiva, Israel.

The observed plant was grown with fertilization rates as follows:

$N:P_2O_5:K_2O$ in the ratio of 5:3:8.

The observed plant was grown at temperatures as follows:

Day maximum: 30 Celsius.

Night minimum: 24 Celsius.

Disease resistance or susceptibility: None observed.
Parentage:
*Male parent.*—Unknown.
*Female parent.*—*Solidago* seedling identified as 3-py-35.
Botanical classification:
*Genus.*—*Solidago.*
*Species.*—*hybrida.*
*Denomination.*—'Dansolitlem'.
Propagation: Stem tip cutting.
Plant:
*Growth habit.*—Compact for the genus.
*Height.*—30–35 cm.
*Width.*—20 cm.
*Plant vigor.*—Moderate for the genus.
*Cold tolerance.*—Hardy at least in USDA Zone 7 (survives minus 15 Celsius).
Root description: Fibrous Roots.
Branches: Single if not pinched, branched from base, 3–6 stems, when pinched (terminal apex removed).
Stem description based on a pinched plant:
*Stem arrangement.*—Rising together from main stem base.
*Number of stems.*—3–6 stems.
*Length.*—35 cm.
*Width.*—5 mm.
*Internode length.*—1.5–2 cm.
Foliage:
*Leaf shape.*—Lanceolate.
*Leaf arrangement.*—Alternate.
*Leaves per stem.*—15–25.
*Leaf texture.*—Smooth.
*Leaf margin.*—Dentate.
*Leaf apex.*—Acute.
*Leaf base.*—Attenuate.
*Venation.*—Pinnate.
*Color of mature leaf* (*both surfaces*).—137C.
*Color of juvenile leaf* (*both surfaces*).—137D.
Petioles:
*Length.*—2 mm.
*Color.*—146D.
Inflorescence:
*Type.*—Capitulum consisting of plume-like panicles with ray and disc florets.
*Form.*—Panicle elongated, individual flowers borne in one side, predominantly upward-facing.
*Length of panicle.*—8–15 cm.
*Width of panicle.*—5–10 cm.
*Buds of inflorescence.*—3 mm in length, 1 mm in width, color 7C.
Ray florets:
*Color* (*upper surface*).—Yellow group 7C.
*Color* (*under surface*).—Yellow group 7D.
*Shape.*—Round.
*Number of ray florets per inflorescence.*—Approximately 10 arranged in one row.
*Dimensions of ray floret.*—1 mm in length, 0.5 mm. in width.
*Apex.*—Obtuse.
*Base.*—Cuneate.
*Margin.*—Entire.
Disc florets:
*Shape.*—Rounded.
*Color* (*mature*).—13A.
*Diameter of disc.*—1 mm.
*Number of discs per flower.*—4–6.
*Dimensions.*—Length, 1 mm; width, 0.2 mm.
Number of flowers per inflorescence: Hundreds.
Natural bloom season: Late summer.
Lastingness of blooms: 10–15 days on or off the plant.
Fading: Yes, Ray florets fade to 6D; Disc florets fade to 6A.
Peduncles:
*Length.*—0.5 cm.
*Color.*—Yellow green group N144 D.
Sepals (involucral bracts):
*Number per inflorescence.*—4–5.
*Dimensions.*—Length, 1 mm; width, 0.2 mm.
*Shape.*—Lanceolate.
*Color.*—Yellow green group N 144 D.
Reproductive organs:
*Anthers.*—4–6 in number, color 13A, length 1 mm.
*Pistils.*—6–10 in number, color 13B, length 1 mm.
*Seeds.*—6–10 in number, color 199C, length 1 mm.

It is claimed:

1. A new and distinct *Solidago* named 'Dansolitlem' substantially as illustrated and described herein.

* * * * *